United States Patent
Salisbury et al.

(10) Patent No.: US 6,838,067 B2
(45) Date of Patent: Jan. 4, 2005

(54) METAMORPHOSED MINERAL COMPOSITIONS HAVING INTERNAL LATTICE DEFECTS AND METHODS OF MAKING

(75) Inventors: Bruce Salisbury, Farmington, NM (US); Vernon D. Pilcher, Kirtland, NM (US)

(73) Assignee: Pinnacle West Capital Corporation, Phoenix, AZ (US)

( * ) Notice: Subject to any disclaimer, the term of this patent is extended or adjusted under 35 U.S.C. 154(b) by 110 days.

(21) Appl. No.: 10/288,014

(22) Filed: Nov. 5, 2002

(65) Prior Publication Data

US 2003/0094118 A1 May 22, 2003

Related U.S. Application Data

(60) Provisional application No. 60/337,879, filed on Nov. 5, 2001.

(51) Int. Cl.⁷ ............................................. C01B 33/26
(52) U.S. Cl. ..................... 423/328.3; 423/324; 423/326
(58) Field of Search ................................ 423/324, 326, 423/328.3; 502/232, 410

(56) References Cited

U.S. PATENT DOCUMENTS

| | | |
|---|---|---|
| 2,469,512 A | 5/1949 | Naugle |
| 4,806,320 A | 2/1989 | Nelson |
| 4,829,036 A | 5/1989 | Nelson et al. |
| 4,980,137 A | 12/1990 | Nelson et al. |
| 5,288,674 A | 2/1994 | Taylor, Jr. |
| 5,376,609 A | 12/1994 | Guile |
| 5,380,506 A | 1/1995 | Taylor, Jr. |
| 5,387,565 A | 2/1995 | Taylor, Jr. |
| 5,505,745 A | 4/1996 | Taylor, Jr. |
| 5,626,689 A | 5/1997 | Taylor, Jr. |
| 5,667,751 A | 9/1997 | Taylor, Jr. |
| 5,709,734 A | 1/1998 | Scholz |
| 6,150,300 A | 11/2000 | Khare |
| 6,225,681 B1 | 5/2001 | Chungpaiboonpatana et al. |
| 6,240,859 B1 | 6/2001 | Jones, Jr. |

FOREIGN PATENT DOCUMENTS

WO   WO 01/79341   10/2001

OTHER PUBLICATIONS

PCT Written Opinion—Nov. 17, 2003.
PCT International Search Report—Apr. 3, 2003.
Database WPI Section Ch, Week 199102 Derwent Publications, Ltd., London, GB Class L03, AN 1991–013974 XP0002235676 & SU 1545 263 A (Irkut Poly), Feb. 23, 1990 abstract.

*Primary Examiner*—Stanley S. Silverman
*Assistant Examiner*—Edward M. Johnson
(74) *Attorney, Agent, or Firm*—Snell & Wilmer, LLP

(57) ABSTRACT

A method of controllably altering the mineral matter transformation of mineral compositions such as, for example, vermiculitic micas, to achieve metamorphosed mineral compositions having specifically desired monatomic lattice defects is provided. Compositions formed in accordance with the method are also provided that exhibit physical properties desirable in a variety of industrial applications, including, for example, control and/or reduction of $NO_x$, $SO_x$, $CO_x$ and other gaseous chemical species from industrial effluents, atmospheric control systems, fabrication and use of chemical detectors, and solid state electronic substrates and devices.

39 Claims, 6 Drawing Sheets

METAMORPHOSED MINERAL COMPOSITIONS HAVING INTERNAL LATTICE DEFECTS AND METHODS OF MAKING

CROSS-REFERENCE TO RELATED APPLICATION

This application claims priority from U.S. Provisional Patent Application Ser. No. 60/337,879, entitled "Metamorphosed Vermiculitic Mica Having Internal Lattice Defects and Methods of Making and Using the Same," filed Nov. 5, 2001.

FIELD OF THE INVENTION

This invention relates generally to a method of controllably altering the mineral matter transformation of certain compounds to achieve mineral compositions exhibiting monatomic crystal lattice defects useful in a variety of applications. More specifically, the invention relates to a method of controllably altering the mineral matter transformation of mineral compositions such as, for example, micas and other silicates, to achieve metamorphosed mineral compositions having specifically desired monatomic lattice defects.

BACKGROUND OF THE INVENTION

Many materials exist in nature that, when heated to a known elevated temperature, will undergo a metamorphic transformation to a different, yet stable and recognizable material that is a potentially useful material in its own form. Typically, the method of affecting this transformation has been to elevate the temperature of the material far above the transformation temperature range point to effectuate a rapid, cataclysmic transformation of the material to a new, metamorphosed state. Through use of this so-called "brute force" method of effecting mineral matter transformations, high volumes of mineral compositions, such as, for example, vermiculitic precursor materials, may be metamorphosed in a short period of time. This process is sometimes referred to as an "exfoliation" process, especially with regard to vermiculitic materials.

Such "brute force" exfoliation methods, however, typically require relatively high energy expenditures, as the temperatures reached by the reaction vessels utilized generally exceed the required temperature for mineral matter transformation by several hundred degrees Farenheit. Moreover, because prior art "brute force" mineral matter transformation techniques are designed for high-throughput operations, they are not generally intended to produce high-quality, carefully controlled metamorphosed materials.

What is needed in the art is a method of controllably interacting with the mineral matter transformation of mineral compositions to enable the selective alteration of material properties through controlled formation of monatomic defects in the crystal lattice of such compositions. It would also be advantageous to achieve such a method while reducing and/or minimizing required energy expenditures.

SUMMARY OF THE INVENTION

While the way in which the present invention addresses the deficiencies and disadvantages of the prior art is described in greater detail below, in general, according to its various aspects, the present invention includes a process for controllably altering the mineral matter transformation of certain compounds to achieve mineral compositions exhibiting certain lattice defects useful in a variety of applications. More specifically, the invention relates to a method of controllably altering the mineral matter transformation of mineral compositions such as, for example, micas and other silicates, to achieve metamorphosed mineral compositions having specifically desired monatomic lattice defects.

Various aspects of the present invention may be applied to processes for making metamorphosed mineral compositions and processes for utilizing metamorphosed mineral compositions. In accordance with an exemplary embodiment, a method of forming a metamorphosed mineral composition having internal lattice defects generally comprises (i) providing a composite material stream comprising up to about 50% by weight of a scavenger material and up to about 95% by weight of a mineral composition, and (ii) heat treating the composite material stream at a temperature of at least about 90% of the mineral matter transformation temperature for the mineral composition in an environment having relatively low excess oxygen to form monatomic defects in the crystal lattice of the mineral composition.

In accordance with another exemplary embodiment of the invention, a method of forming a metamorphosed vermiculitic mica having internal lattice defects comprises (i) providing a composite material stream comprising up to about 50% by weight of an oxygen and/or halide scavenger material and up to about 95% by weight of a vermiculitic precursor material, and (ii) heat treating the composite material stream at a temperature of at least about 90% of the mineral matter transformation temperature for the vermiculitic precursor material in an environment having relatively low excess oxygen. In accordance with an exemplary embodiment of the invention, a method of forming metamorphosed phlogopite (i.e., magnesium mica) is provided that comprises heat treating a composite material comprising maghemite and phlogopite in a reducing environment.

In accordance with one aspect of an exemplary embodiment of the invention, a metamorphosed mineral composition, such as a metamorphosed vermiculitic mica, is provided that generally comprises (i) up to about 50% by weight of a suitably adapted oxygen and/or halide scavenger; (ii) up to about 95% by weight of a mineral composition, such as, for example, a vermiculitic material; and (iii) an effective number of monatomic defects in the crystal lattice of the metamorphosed mineral composition. In accordance with other embodiments of the invention, metamorphosed mineral compositions formed in accordance with the invention may be combined with a suitably adapted substrate to form the basis of a variety of solid-state devices.

In accordance with various other embodiments of the present invention, metamorphosed mineral compositions also may be utilized in the control and/or reduction of $NO_x$, $SO_x$ and/or $CO_x$ from combustion gases, the control and/or reduction of various other gaseous components from combustion gases, and the fabrication and use of monatomic chemical detectors. By way of example, such applications for the novel compositions of matter prepared in accordance with the present invention are provided as specific enabling disclosures that may be generalized by those skilled in the art. Indeed, various other applications of the disclosed metamorphosed mineral compositions and/or methods of making and/or methods of using metamorphosed mineral compositions having internal lattice defects are foreseeable in accordance with the present invention.

DETAILED DESCRIPTION

Figure 1:
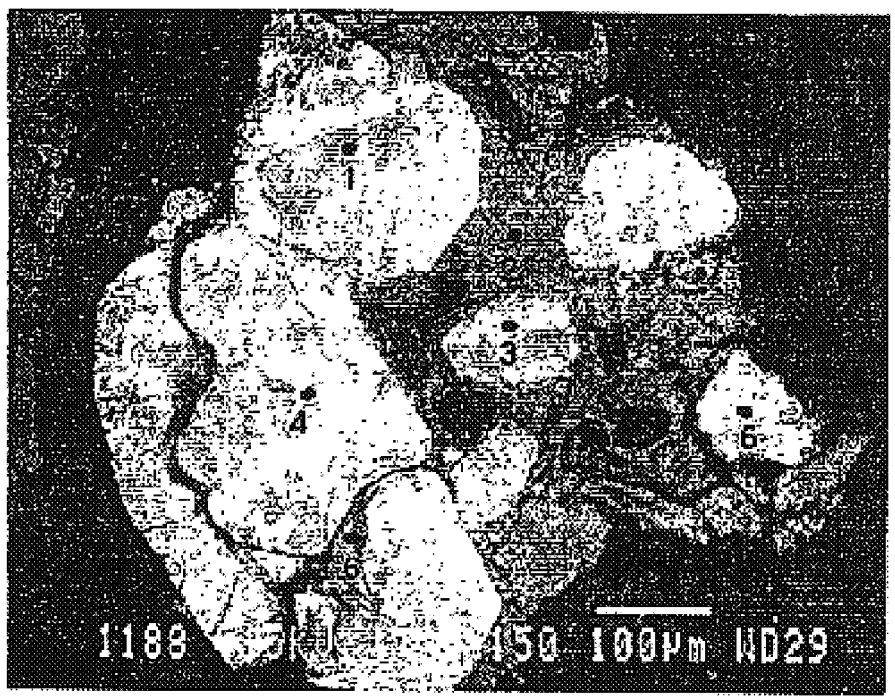
FIG. 1 is an exemplary electron image of metamorphosed phlogopite, also referred to herein as "Rinkite," showing analysis points 1–6 as summarized in Table 1.

The following detailed description is of various exemplary embodiments of the invention and the inventors' conception of the best mode, and is not intended to limit the scope, applicability or configuration of the invention in any way. Rather, the following detailed description is intended to provide a convenient illustration for implementing various exemplary embodiments of the invention. As will become apparent, various changes may be made in the function and arrangement of the elements described hereinbelow without departing from the spirit and scope of the invention.

Method of Manufacture

In general, according to one embodiment of the present invention, a method for controllably altering the mineral matter transformation of mineral compositions to achieve metamorphosed mineral compositions having specifically desired monatomic lattice defects is provided. In accordance with an exemplary embodiment, a method of forming a metamorphosed mineral composition having internal lattice defects generally comprises (i) providing a composite material stream comprising up to about 50% by weight of a scavenger material and up to about 95% by weight of a mineral composition, and (ii) heat treating the composite material stream at a temperature of at least about 90% of the mineral matter transformation temperature for the mineral composition in an environment having relatively low excess oxygen.

Methods in accordance with various embodiments of the present invention advantageously exploit the mechanism of mineral matter transformation, which leaves the developing lattice structure of the mineral composition vulnerable to the introduction of defects as the transformation takes place. In the relatively narrow temperature range defined by a mineral composition's tendency to undergo a mineral matter transformation at an elevated temperature, the present inventors have achieved the ability to interfere with the molecular structure of mineral compositions by removing or inserting individual atoms into the crystal lattice—thus forming monatomic lattice defects therein—in a manner that is highly controllable, predictable, and repeatable. In contradistinction to prior art "brute force" oxidation and exfoliation methods for forming materials such as vermiculitic micas, which generally require relatively high energy expenditures, the methods disclosed in accordance with the present invention require relatively low energy to form the desired monatomic lattice defects. Stated another way, the methods disclosed in accordance with the present invention require heat treatment at temperatures approximately 500–800° F. lower than heat treatment temperatures employed in prior art processes. In further contradistinction to prior art methods of "brute force" interference with mineral matter transformation, in accordance with the present invention, the removal and/or insertion of atoms from or into the crystal lattice of a mineral composition can be precisely controlled, thus enabling precision engineering of desired monatomic lattice defects therein.

Mineral compositions exhibit unique mineral matter transformation characteristics, namely, unique temperature ranges within which mineral matter transformation occurs. Thus, depending upon the mineral composition subjected to the methods of the present invention, different heat treatment parameters may be required to achieve the benefits of the present invention. For example, while phlogopite undergoes mineral matter transformation at temperatures generally ranging from about 1200° F. to about 1600° F., aluminum silicates tend to undergo mineral matter transformation at temperatures ranging from about 1450° F. to about 2400° F. (the specific temperature range being dependent upon the exact composition of the material). Mineral compositions that are suitable for use in connection with the various embodiments of the present invention include, but are not limited to, micas, most aluminum silicates, silicon and silicon compounds, and other mineral compositions comprising an alkali metal and/or a semi-metal oxide that have known and demonstrable mineral matter transformation properties. Moreover, skilled artisans will appreciate that the use of an inert gas stream and/or standard provisions for heating under at least partial vacuum, in addition to other methods well known in the art, may be used to substantially realize an environment having relatively low excess oxygen. As used herein, the term "low excess oxygen" refers to environmental conditions having less than about 5% excess oxygen, preferably from about 1% to about 3% excess oxygen, and more preferably substantially no excess oxygen (i.e., substantially inert conditions).

Any reaction vessel or other apparatus suitable for providing the required environmental conditions to effectuate the mineral matter transformation process in accordance with various exemplary embodiments of the invention may be employed. In accordance with one embodiment, the reaction vessel comprises, for example, an oven that is capable of reaching temperatures equal to or above the mineral matter transformation temperature(s) of the mineral compositions desired to be heat treated therein. Moreover, the reaction vessel should be adapted to maintain an inert atmosphere within the vessel during the mineral matter transformation process and to maintain contact between the scavenger material and the mineral composition to be heat treated. Preferably, the internal temperature of the reaction vessel may be carefully controlled, such as, for example, by a feedback control device incorporating one or more thermocouples, so as to optimize the development of the preferred lattice structure of the metamorphosed mineral composition in the inert atmosphere. In accordance with another embodiment of the invention, a coal fired boiler may be utilized at a select point in the boiler where the temperatures are suitable to enable the transformation of a mineral composition introduced into the boiler, and the oxygen level of the flue gas flowing therethrough is low enough to effect an inert atmosphere suitable for a controlled mineral matter transformation.

In accordance with one aspect of an exemplary embodiment of the invention, during the heat treatment of the composite material stream at a temperature of at least about 90% of the mineral matter transformation temperature for the mineral composition component of the stream, the scavenger material removes or introduces individual atoms to the crystal lattice of the mineral composition, resulting in monatomic crystal lattice defects. In accordance with an exemplary embodiment of the invention, the mineral composition is maintained at the desired heat treating temperature for at least about one (1) minute, preferably from about one to about five minutes.

In accordance with an exemplary embodiment of the invention, the scavenger material comprises a suitably adapted oxygen and/or halide scavenger. Suitably adapted oxygen and/or halide scavengers may include, for example, any oxygen and/or halide scavengers now known or hereafter derived by those skilled in the art, such as, for example, maghemite ($Fe_2O_3$), aluminum, aluminum silicate, silicate, elemental carbon and/or similar materials.

Where an oxygen scavenger is used, such as the use of maghemite in combination with the mineral composition phlogopite, the oxygen scavenger serves to remove oxygen atoms from the crystal lattice of the mineral composition, thus creating monatomic defects in the crystal lattice. Such monatomic defects, as result from the removal of atoms from the crystal lattice, are characterized by "holes" in the crystal lattice or the absence of a particular monatomic species in a lattice position otherwise populated in a geometrically corresponding position of the lattice wherein the local and/or global lattice geometry remains substantially unaltered. Monatomic defects resulting from the introduction of monatomic species into the crystal lattice of a mineral composition are characterized by interstitial atom point defects or substitutional atom defects, which are localized disruptions of the otherwise perfect geometrical arrangement of the surrounding atoms in the crystal lattice.

In accordance with an aspect of another exemplary embodiment wherein a halide scavenger may be substituted for an oxygen scavenger to introduce corresponding lattice defects and wherein one or more halide atoms (such as, for example, F, Cl, I, Br) are removed from the crystal lattice, thereby producing a metamorphosed vermiculitic mica having at least partial selectivity to the particular halide of interest. Those skilled in the art will appreciate that various other defects selective to various other chemical species may be similarly so introduced.

Such desirable monatomic defects may comprise, for example, oxygen defects, halide defects, and/or any other monatomic defects suitably adapted to demonstrate at least partially selective activity of the composite material formed thereby to a particular chemical species, and/or to prepare the composite material formed thereby for at least partially selective doping or substitutive population and/or eliminative population of at least an effective number of defect sites.

Preferably, up to about 50% by weight of a scavenger material is utilized in accordance with one aspect of this embodiment of the invention. More preferably about 5% to about 40% by weight of a scavenger material and most preferably in the range of about 10% to about 30% by weight of a scavenger material is used.

In accordance with another aspect of this embodiment of the invention, the composite material preferably includes up to about 95% by weight of a mineral composition, and more preferably from about 50% to about 95% by weight of a mineral composition. Most preferably, from about 70% to about 90% by weight of a mineral composition is used. As used herein, "mineral composition" may include any mica, aluminum silicate, silicon or silicon compound, and/or other mineral composition comprising an alkali metal and/or a semi-metal oxide that has known and demonstrable mineral matter transformation properties.

In another aspect of an exemplary embodiment of the invention, the mineral composition and/or the scavenger material may be comminuted before heat treating to increase the surface area of the particles in the composite material stream. Comminution may be achieved by any of a variety of mechanisms and/or devices known to those skilled in the art, such as, for example, ball milling, tower milling, wet grinding, attrition milling, stirred milling, and the like. Any techniques now known or hereafter developed that may achieve the desired result of reducing the particle size of the mineral species may be utilized in accordance with this aspect.

In accordance with another exemplary embodiment of the invention, a method of forming a metamorphosed vermiculitic mica having internal lattice defects comprises (i) providing a composite material stream comprising up to about 50% by weight of an oxygen and/or halide scavenger material and up to about 95% by weight of a vermiculitic precursor material, and (ii) heat treating the composite material stream at a temperature of at least about 90% of the mineral matter transformation temperature for the vermiculitic precursor material in an environment having relatively low excess oxygen.

Preferably, up to about 50% by weight of a suitably adapted oxygen and/or halide scavenger is utilized in accordance with one aspect of an exemplary embodiment of the invention. More preferably about 5% to about 40% by weight of a suitably adapted oxygen and/or halide scavenger and most preferably in the range of about 10% to about 30% by weight of a suitably adapted oxygen and/or halide scavenger is used.

In accordance with another aspect of one embodiment of the invention, the composite material preferably includes up to about 95% by weight of a vermiculitic precursor material, and more preferably from about 50% to about 95% by weight of a vermiculitic precursor material. Most preferably, from about 70% to about 90% by weight of a vermiculitic precursor material is used. As used herein, "vermiculitic precursor material" includes any vermiculitic precursor materials now known or hereafter derived by those skilled in the art, such as, for example, vermiculite ($Mg_x(Mg,Fe)_3(Si,Al)_4O_{10}(OH)_2$), phlogopite ($KMg_3(Si_3Al)O_{10}(OH)_2$), biotite, ganterite and other micas and silicate minerals.

In accordance with another aspect of an embodiment of the invention, the composite material stream is heat treated at a temperature of at least 90% of the mineral matter transformation temperature for the composite material in an environment having relatively low excess oxygen. In one embodiment, the heat treatment temperature is from about 1200° F. to about 1600° F. For the purposes of the present invention, a "vermiculitic precursor material" shall be understood to include any material that upon heating and/or the application of pressure may be at least partially transformed to a different thermodynamic state to substantially demonstrate the properties of a vermiculitic material, such as, for example, vermiculite.

In accordance with yet another exemplary embodiment of the present invention, metamorphosed phlogopite demonstrating monatomic oxygen defects may be obtained by heat treating a composite material comprising maghemite and phlogopite at a temperature of from about 1200° F. to about 1600° F. in an environment having relatively low excess oxygen. In accordance with one aspect of this exemplary embodiment, the composite material preferably includes up to about 50% by weight of maghemite ($Fe_2O_3$). More preferably, about 5% to about 40% by weight of maghemite, and most preferably, from about 10% to about 30% by weight of a maghemite is present in the composite.

In accordance with another aspect of this embodiment of the invention, the composite material preferably includes up to about 95% by weight, and more preferably from about 50% to about 95% by weight of phlogopite. Most preferably, phlogopite is present in the composite in an amount from about 70% to about 90% by weight.

In the case of using phlogopite as a vermiculitic precursor material, it is believed that the phlogopite transforms under oxidation inhibition conditions to a vermiculite material demonstrating the desired lattice defects; which in the case of using maghemite as the scavenger corresponds to defects demonstrating at least partial selectivity to oxygen.

Compositions of Matter

In accordance with another aspect of an exemplary embodiment of the invention, a metamorphosed mineral composition is provided. As formed in accordance with the above-described methods, the metamorphosed mineral composition generally comprises (i) up to about 50% by weight of a scavenger material; (ii) up to about 95% by weight of a mineral composition; and (iii) an effective number of monatomic defects in the crystal lattice of the metamorphosed mineral composition.

In accordance with a preferred embodiment of the invention, a metamorphosed mineral composition, such as a metamorphosed vermiculitic mica, is provided that generally comprises (i) up to about 50% by weight of a suitably adapted oxygen and/or halide scavenger; (ii) up to about 95% by weight of a vermiculitic precursor material; and (iii) an effective number of monatomic defects in the crystal lattice of the metamorphosed vermiculitic material.

In accordance with one aspect of this preferred embodiment, preferably up to about 50% by weight of a suitably adapted oxygen and/or halide scavenger, more preferably from about 5% to about 40% by weight of a suitably adapted oxygen and/or halide scavenger, and most preferably from about 10% to about 30% by weight of a suitably adapted oxygen and/or halide scavenger is present in the composition. Suitably adapted oxygen and/or halide scavengers may include, for example, any oxygen and/or halide scavengers now known or hereafter derived by those skilled in the art, maghemite ($Fe_2O_3$), aluminum, aluminum silicate, silicate, elemental carbon and/or similar materials.

In accordance with another aspect of this preferred embodiment, preferably up to about 95% by weight of a vermiculitic precursor material, more preferably from about 50% to about 95% by weight, and most preferably from about 70% to about 90% by weight of a vermiculitic precursor material is present in the composition. As used herein, "vermiculitic precursor material" includes any vermiculitic precursor materials now known or hereafter derived by those skilled in the art, such as, for example, vermiculite ($Mg_x(Mg,Fe)_3(Si,Al)_4O_{10}(OH)_2$), phlogopite ($KMg_3(Si_3Al)O_{10}(OH)_2$), biotite, ganterite and other micas and silicate minerals.

Monatomic defects in accordance with this exemplary embodiment shall be understood to include monatomic "holes" in the crystal lattice structure or the absence of a particular monatomic species in a lattice position otherwise populated in a geometrically corresponding position of the lattice wherein the local and/or global lattice geometry remains substantially unaltered. An "effective number" of monatomic defects shall be understood to include any quantity of defects suitably adapted for the material's specific intended purpose such as, for example, reduction of chemical species from a combustion gas stream, detection of monatomic chemical species, fabrication of semiconductor and other solid-state devices, and other applications of the metamorphosed compositions of the present invention. The desired number and/or distribution of such defects will depend upon the chosen application for the metamorphosed material, and may be determined via trivial experimentation by those skilled in the art. In accordance with one aspect of an exemplary embodiment of the invention, the number of monatomic defects is at least about 2% by volume, preferably from about 2% to about 10% by volume, and more preferably from about 3% to about 8% by volume of the mineral composition.

In accordance with various embodiments of the present invention, such monatomic defects may comprise, for example, oxygen defects, halide defects (F, Cl, I, Br); and/or any other monatomic defects suitably adapted (i) to demonstrate at least partially selective activity of the composite material formed thereby to a particular chemical species, and/or (ii) to prepare the composite material formed thereby for at least partially selective doping or substitutive population and/or eliminative population of at least an effective number of defect sites.

The metamorphosed vermiculitic micas, in accordance with the present invention, may further optionally comprise any material suitably adapted as a substrate, any material suitably adapted to provide an appropriate local or global lattice geometry and/or geometric feature; hematite ($Fe_2O_3$); feldspar (such as, for example, $Na(AlSi_3O_8)$—$Ca(Al_2Si_2O_8)$); biotite; ganterite and/or substantial equivalents thereof.

Metamorphosed mineral compositions provided in accordance with various embodiments of the present invention were subjected to morphological analyses as set forth in the following Examples.

EXAMPLE 1

Metamorphosed phlogopite, referred to herein as "Rinkite," was produced by the heat treatment of a composite of maghemite and phlogopite in accordance with the various aspects of the invention described above.

Samples of the metamorphosed phlogopite were mounted in epoxy resin and allowed to harden. These samples were then cross-sectioned and polished for scanning electron microscopy morphological analysis. In addition, the metamorphosed phlogopite samples were mounted on double-stick tape for morphological analysis. This analysis provided spectra, morphological analysis images and elemental compositions of selected regions in the deposits. The analysis was conducted using back-scattered electron imaging (BEI) that distinguishes between materials of different atomic number.

In general, the morphological analysis results for one sample of metamorphosed phlogopite indicated the presence of several types of particles. One group comprised mainly aluminum, silicon, calcium, iron and oxygen. The second group comprised primarily particles containing high iron with correspondingly low levels of silicon and oxygen. Gold-colored particles in the metamorphosed phlogopite further comprised varying levels of silicon, potassium, iron, and oxygen as well as sodium, magnesium, aluminum, and titanium. No significant levels of sulfur were observed. The edges of certain iron-rich component particles were found to be at least partially depleted in oxygen, while the inner parts of the particles had higher levels of oxygen, despite the fact that the exposure to flue gases would have been believed to cause a corresponding increase in the level of oxygen on the surface of the particles.

Table 1 summarizes the results of the morphological analysis for metamorphosed phlogopite. The results of this analysis are expressed as weight percentages of the composition in Table 1, normalized to 100%.

TABLE 1

| Point | Description | Na | Mg | Al | Si | P | S | Cl | K | Ca | Ti | V | Cr | Mn | Fe | Ba | O |
|---|---|---|---|---|---|---|---|---|---|---|---|---|---|---|---|---|---|
| 1 | Gray strip | 0.00 | 0.00 | 0.00 | 0.00 | 19.13 | 0.00 | 1.33 | 0.82 | 44.38 | 0.00 | 0.00 | 0.00 | 0.00 | 0.53 | 0.00 | 33.81 |
| 2 | Dark matrix | 0.00 | 1.31 | 8.71 | 33.71 | 0.00 | 0.00 | 0.40 | 2.62 | 1.28 | 2.26 | 0.00 | 0.42 | 0.00 | 8.05 | 0.00 | 41.24 |
| 3 | Gray area | 0.00 | 0.00 | 0.00 | 0.00 | 15.38 | 0.00 | 1.02 | 0.92 | 32.12 | 0.00 | 0.00 | 0.00 | 0.00 | 0.00 | 0.00 | 50.56 |
| 4 | Bright area | 0.00 | 0.69 | 0.00 | 2.49 | 0.00 | 0.00 | 0.00 | 0.27 | 0.00 | 1.02 | 0.00 | 0.00 | 0.59 | 77.38 | 0.00 | 17.56 |
| 5 | Bright ptcl | 0.00 | 0.00 | 2.02 | 1.44 | 0.00 | 0.00 | 0.38 | 0.00 | 0.00 | 4.93 | 0.00 | 0.00 | 0.82 | 72.71 | 0.00 | 17.71 |
| 6 | Dark strip | 0.00 | 6.12 | 0.94 | 33.52 | 0.00 | 0.58 | 0.00 | 1.05 | 9.28 | 0.00 | 0.00 | 0.00 | 0.00 | 14.21 | 0.00 | 34.30 |
| 7 | Bright ptcl | 0.00 | 1.21 | 1.51 | 2.31 | 0.00 | 0.00 | 0.22 | 0.00 | 0.00 | 3.05 | 0.00 | 0.67 | 0.00 | 69.06 | 0.00 | 21.97 |
| 8 | Bright ptcl | 0.00 | 0.99 | 0.81 | 0.78 | 0.00 | 0.00 | 0.00 | 0.00 | 0.00 | 4.35 | 0.00 | 0.31 | 1.82 | 75.18 | 0.00 | 15.76 |
| 9 | Bright ptcl | 0.00 | 1.58 | 0.89 | 2.43 | 0.00 | 0.00 | 0.00 | 0.00 | 0.25 | 3.85 | 0.00 | 0.00 | 1.11 | 70.76 | 0.00 | 19.14 |
| 10 | Bright ptcl | 0.00 | 1.22 | 0.00 | 4.46 | 0.00 | 0.00 | 0.00 | 0.00 | 0.57 | 3.03 | 0.00 | 0.66 | 0.00 | 76.91 | 0.00 | 13.16 |
| 11 | Bright ptcl | 0.00 | 0.00 | 0.00 | 4.55 | 0.00 | 0.00 | 0.00 | 0.00 | 0.26 | 0.96 | 0.00 | 0.28 | 0.00 | 76.93 | 0.00 | 17.03 |
| 12 | Bright ptcl | 0.00 | 0.98 | 1.21 | 0.62 | 0.00 | 0.00 | 0.23 | 0.27 | 0.00 | 3.89 | 0.00 | 0.30 | 1.64 | 73.90 | 0.00 | 16.95 |
| 13 | Metallic ptcl | 0.00 | 7.77 | 5.56 | 16.85 | 0.00 | 0.00 | 0.36 | 13.06 | 0.36 | 7.14 | 0.00 | 0.00 | 1.45 | 37.60 | 0.00 | 9.85 |
| 14 | Metallic ptcl | 0.00 | 9.66 | 7.51 | 21.83 | 0.00 | 0.00 | 0.39 | 12.19 | 0.32 | 7.05 | 0.00 | 0.00 | 0.00 | 32.86 | 0.00 | 8.18 |
| 15 | Metallic ptcl | 0.00 | 11.89 | 7.52 | 17.79 | 0.00 | 0.00 | 0.00 | 5.44 | 0.00 | 2.42 | 0.00 | 0.33 | 0.00 | 9.29 | 0.00 | 45.32 |
| 16 | Metallic ptcl | 0.00 | 12.49 | 8.95 | 24.50 | 0.00 | 0.00 | 0.15 | 6.15 | 0.25 | 2.45 | 0.00 | 0.00 | 0.42 | 8.53 | 0.00 | 36.11 |
| 17 | Edge of ptcl | 0.92 | 0.00 | 9.80 | 51.12 | 0.00 | 0.00 | 0.00 | 6.43 | 0.76 | 0.00 | 0.00 | 0.00 | 0.00 | 0.73 | 0.86 | 29.39 |
| 18 | Center of ptcl | 0.00 | 12.45 | 8.58 | 24.43 | 0.00 | 0.00 | 0.46 | 6.91 | 0.63 | 2.43 | 0.00 | 0.00 | 0.00 | 8.50 | 0.00 | 35.61 |
| 19 | Edge of ptcl | 0.00 | 13.14 | 9.09 | 26.24 | 0.00 | 0.00 | 0.00 | 9.25 | 0.00 | 4.64 | 0.95 | 0.00 | 0.00 | 13.01 | 0.00 | 23.67 |
| 20 | Edge of ptcl | 0.00 | 12.43 | 11.24 | 31.78 | 0.00 | 0.00 | 0.00 | 9.27 | 0.32 | 4.10 | 0.61 | 0.00 | 0.00 | 13.86 | 0.00 | 16.39 |
| 21 | Edge of ptcl | 0.00 | 1.24 | 4.96 | 16.73 | 0.00 | 0.00 | 0.00 | 20.20 | 0.00 | 11.65 | 0.00 | 0.00 | 0.00 | 45.23 | 0.00 | 0.00 |
| 22 | Edge of ptcl | 0.00 | 3.78 | 10.26 | 34.45 | 0.00 | 0.00 | 0.00 | 15.55 | 0.96 | 6.36 | 0.78 | 0.00 | 0.00 | 27.85 | 0.00 | 0.00 |
| 23 | Bright streak | 0.00 | 8.22 | 8.92 | 18.38 | 0.00 | 0.00 | 0.00 | 3.10 | 0.68 | 3.53 | 1.21 | 0.00 | 0.00 | 5.13 | 30.98 | 19.85 |
| 24 | Bright streak | 0.00 | 4.15 | 2.50 | 9.20 | 0.00 | 0.00 | 0.58 | 5.64 | 1.28 | 8.93 | 1.28 | 0.00 | 0.00 | 11.59 | 51.09 | 3.77 |
| 25 | Bright spot | 0.00 | 9.14 | 5.77 | 14.96 | 0.00 | 0.00 | 0.26 | 3.78 | 0.41 | 1.17 | 0.00 | 0.00 | 0.00 | 42.26 | 0.00 | 22.24 |
| 26 | Bright streak | 0.00 | 2.43 | 2.90 | 14.39 | 0.00 | 0.00 | 0.00 | 7.04 | 1.40 | 7.35 | 0.88 | 0.00 | 0.00 | 13.46 | 46.89 | 3.26 |
| 27 | Edge Fe-rich ptcl | 0.00 | 1.44 | 0.00 | 1.06 | 0.00 | 0.00 | 0.43 | 0.20 | 0.25 | 4.56 | 0.00 | 0.00 | 1.16 | 80.44 | 0.00 | 10.46 |
| 28 | Center of ptcl | 0.00 | 0.00 | 1.45 | 1.17 | 0.00 | 0.00 | 0.00 | 0.00 | 0.00 | 4.74 | 0.00 | 0.00 | 1.15 | 81.35 | 0.00 | 10.13 |
| 29 | Edge Fe-rich ptcl | 0.00 | 0.77 | 0.77 | 0.67 | 0.00 | 0.00 | 0.00 | 0.00 | 0.00 | 4.28 | 0.00 | 0.59 | 1.61 | 75.17 | 0.00 | 16.13 |
| 30 | Center of ptcl | 0.00 | 1.10 | 1.59 | 3.60 | 0.00 | 0.00 | 0.59 | 0.00 | 0.56 | 5.26 | 0.00 | 0.00 | 1.85 | 65.84 | 0.00 | 19.61 |
| 31 | Edge Fe-rich ptcl | 0.00 | 0.99 | 1.87 | 1.70 | 0.00 | 0.00 | 0.44 | 0.00 | 0.00 | 3.65 | 0.00 | 0.00 | 0.94 | 77.57 | 0.00 | 12.84 |
| 32 | Center of ptcl | 0.00 | 1.39 | 1.00 | 2.34 | 0.00 | 0.00 | 0.00 | 0.00 | 0.42 | 2.68 | 0.00 | 0.00 | 2.10 | 71.33 | 0.00 | 18.73 |
| 33 | Edge Fe-rich ptcl | 0.00 | 0.91 | 1.03 | 1.27 | 0.40 | 0.00 | 0.00 | 0.00 | 0.00 | 4.59 | 0.00 | 0.00 | 0.00 | 91.81 | 0.00 | 0.00 |
| 34 | Edge Fe-rich ptcl | 0.00 | 0.00 | 1.26 | 2.65 | 0.00 | 0.00 | 0.00 | 0.42 | 0.00 | 2.79 | 0.00 | 0.84 | 1.01 | 81.90 | 0.00 | 9.14 |
| 35 | Edge Fe-rich ptcl | 0.00 | 1.44 | 2.62 | 0.67 | 0.00 | 0.00 | 0.00 | 0.00 | 0.00 | 4.15 | 0.00 | 0.00 | 2.62 | 66.77 | 0.00 | 21.74 |
| 36 | Edge Fe-rich ptcl | 0.00 | 3.03 | 1.65 | 1.78 | 0.00 | 0.00 | 0.00 | 0.00 | 0.00 | 3.86 | 0.00 | 0.00 | 0.00 | 57.82 | 0.00 | 31.86 |
| 37 | Edge Fe-rich ptcl | 0.00 | 0.00 | 1.19 | 3.42 | 0.00 | 0.00 | 0.00 | 0.00 | 0.00 | 2.08 | 0.00 | 0.00 | 0.00 | 85.46 | 0.00 | 7.85 |
| 38 | Edge Fe-rich ptcl | 0.00 | 1.33 | 0.00 | 2.60 | 0.00 | 0.00 | 0.89 | 0.00 | 0.00 | 2.19 | 0.00 | 0.00 | 0.00 | 85.63 | 0.00 | 7.36 |
| 39 | Edge Fe-rich ptcl | 0.00 | 1.40 | 0.00 | 5.24 | 0.00 | 0.00 | 0.00 | 0.00 | 0.00 | 2.64 | 0.00 | 0.62 | 0.00 | 77.39 | 0.00 | 12.70 |
| 40 | Dark area in ptcl | 0.00 | 0.00 | 1.11 | 0.38 | 20.58 | 0.00 | 1.40 | 1.24 | 40.50 | 0.00 | 0.00 | 0.00 | 0.00 | 0.76 | 0.00 | 34.03 |
| Avg | All Analyses | 0.03 | 4.02 | 3.95 | 13.11 | 1.08 | 0.02 | 0.23 | 4.07 | 3.02 | 3.80 | 0.18 | 0.11 | 0.52 | 41.79 | 4.06 | 20.02 |

Figure 2:
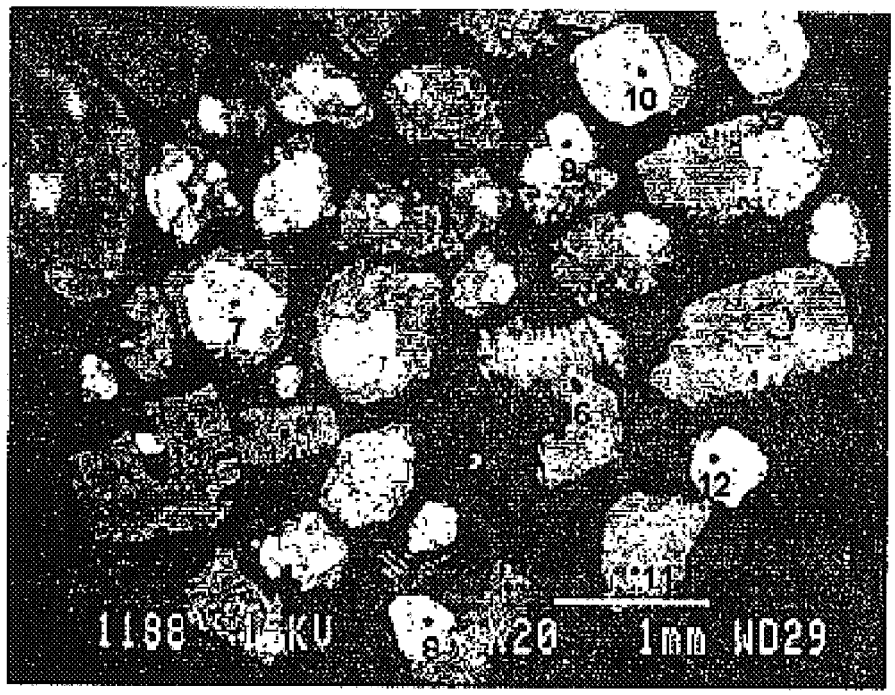
FIG. 2 is an exemplary backscattered electron image of Rinkite showing analysis points 7–16 as summarized in Table 1.
Figure 3:
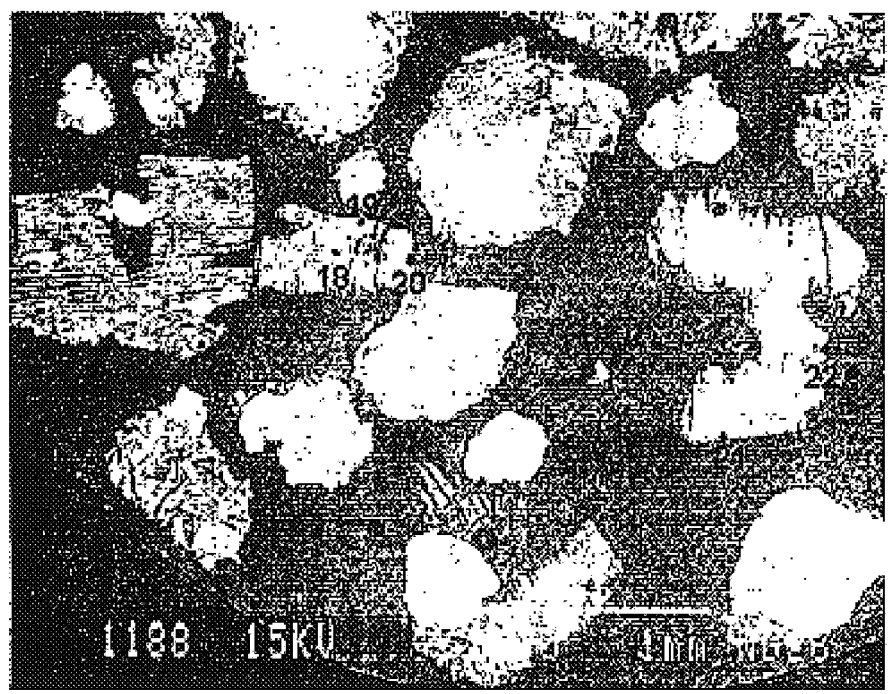
FIG. 3 is an exemplary backscattered electron image of Rinkite showing analysis points 17–22 as summarized in Table 1.
Figure 4:
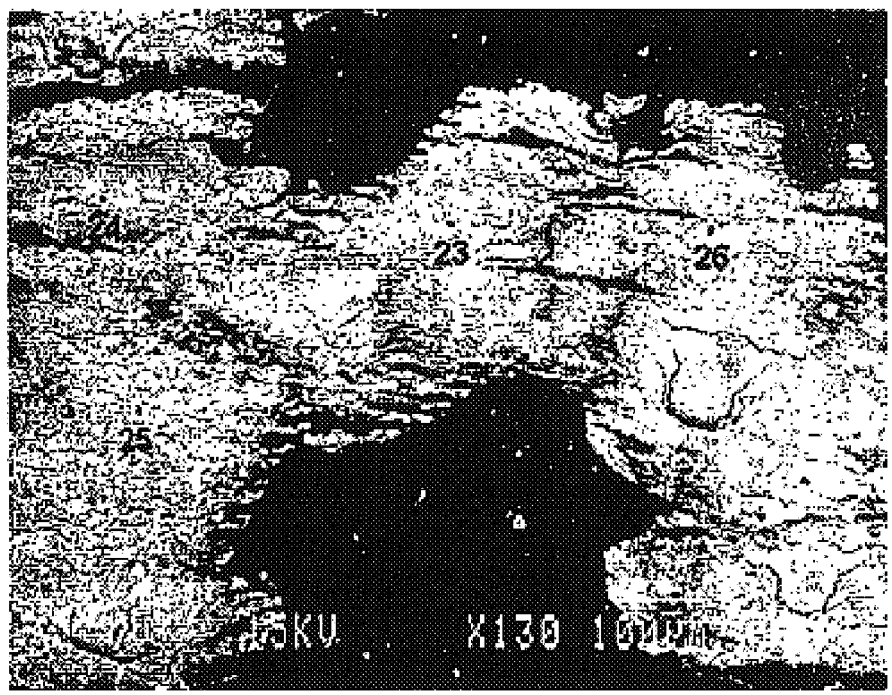
FIG. 4 is an exemplary backscattered electron image of Rinkite showing analysis points 23–26 as summarized in Table 1.
Figure 5:
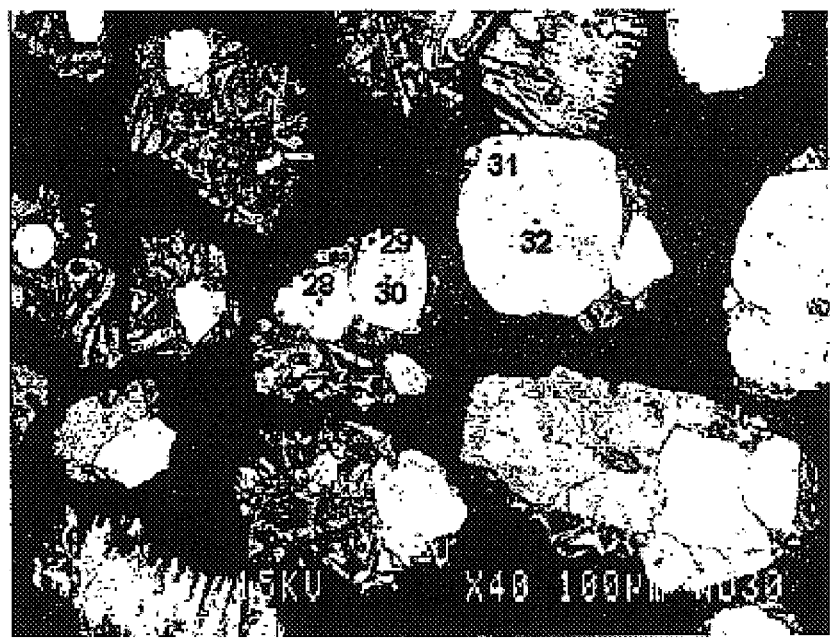
FIG. 5 is an exemplary backscattered electron image of Rinkite showing analysis points 27–2 as summarized in Table 1.
Figure 6:
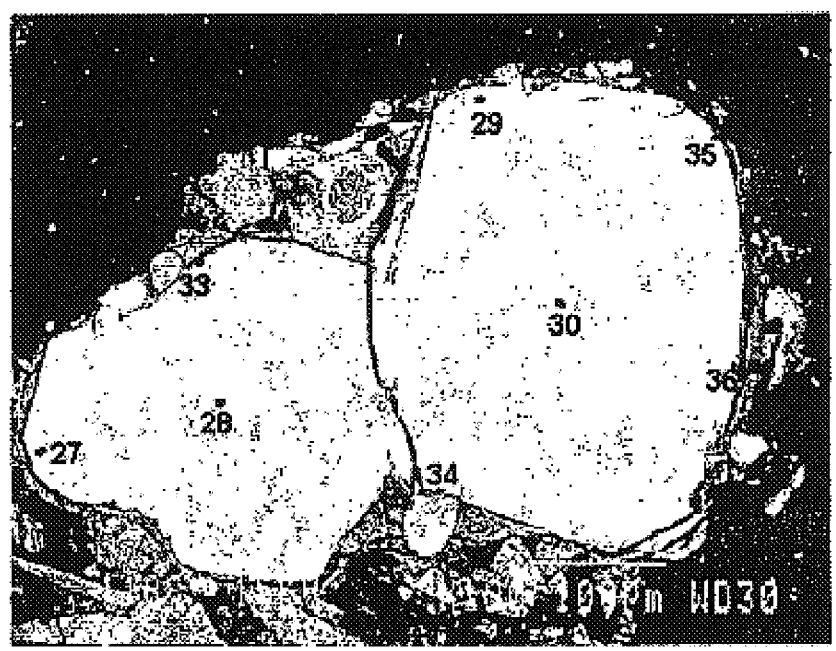
FIG. 6 is an exemplary backscattered electron image of Rinkite showing analysis points 27–30 and 35–36 as summarized in Table 1.
Figure 7:
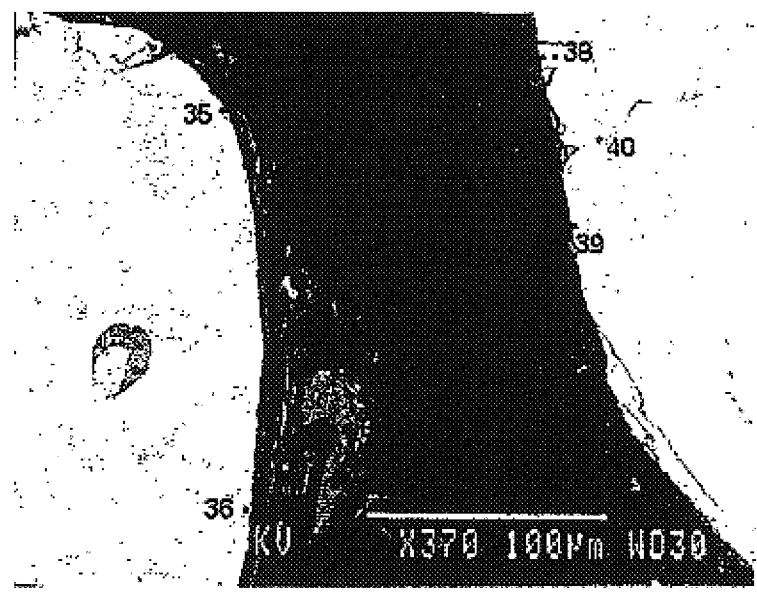
FIG. 7 is an exemplary backscattered electron image of Rinkite showing analysis points 35–40 as summarized in Table 1.

FIG. 1 is an exemplary backscattered electron image of the Rinkite sample showing analysis points 1–6 as summarized in Table 1. An exemplary backscattered electron image of the Rinkite sample showing analysis points 7–16 is provided in FIG. 2. FIG. 3 shows analysis points 17–22. Analysis points 23–26 are shown in the image of FIG. 4. FIG. 5 shows analysis points 27–32; FIG. 6 shows analysis points 27–30 and 35–36; and FIG. 7 shows analysis points 35–40.

EXAMPLE 2

Metamorphosed phlogopite, referred to herein as "Rinkite," was produced by the heat treatment of a composite of maghemite and phlogopite in accordance with the various aspects of the invention described above.

Figure 8:
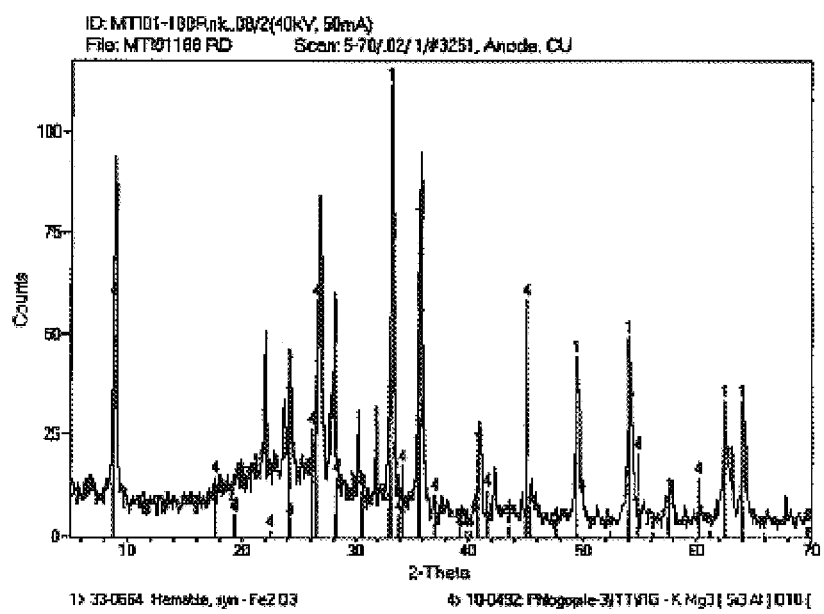
FIG. 8 is an exemplary x-ray diffraction scan for Rinkite showing hematite and phlogopite peaks.
Figure 9:
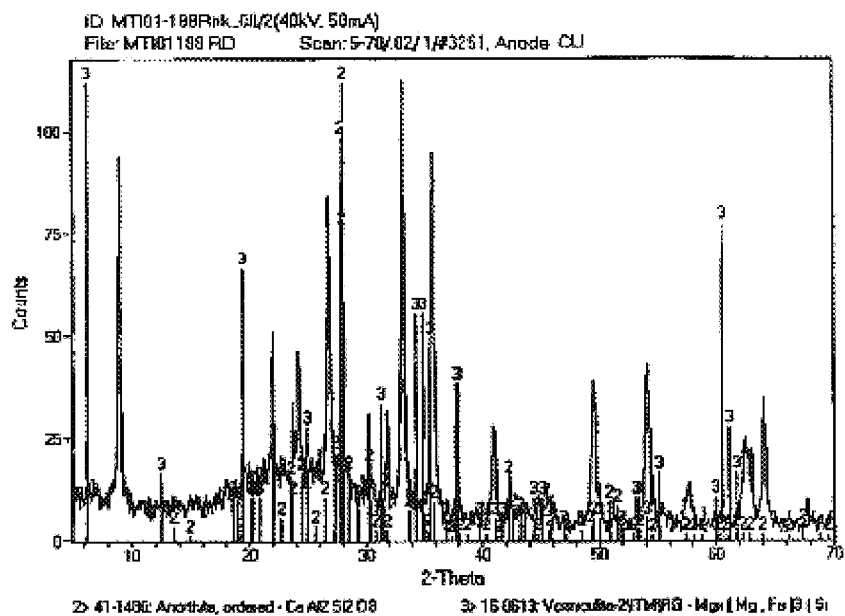
FIG. 9 is an exemplary x-ray diffraction scan for Rinkite showing vermiculite peaks.
Figure 10:
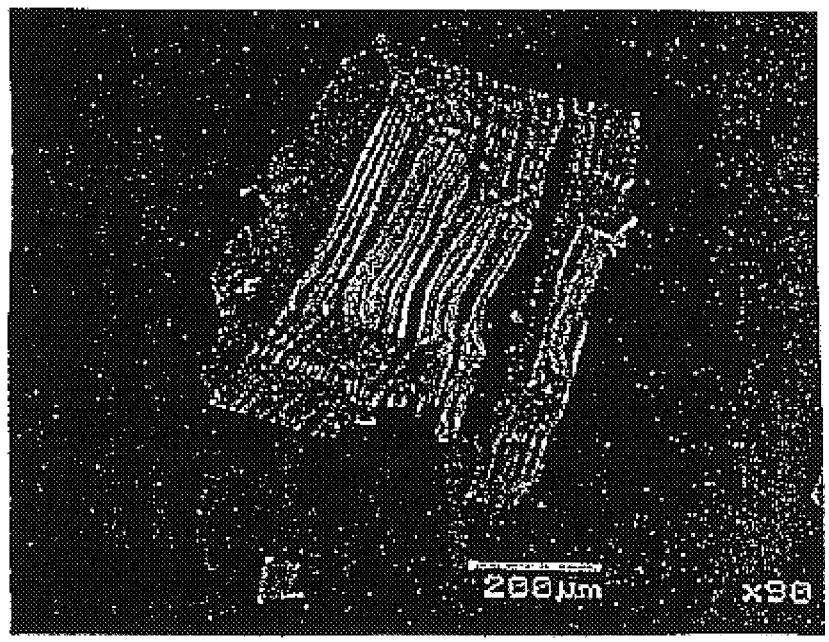
FIG. 10 is an exemplary x-ray diffraction photograph of vermiculite in Rinkite under unheated conditions.
Figure 11:
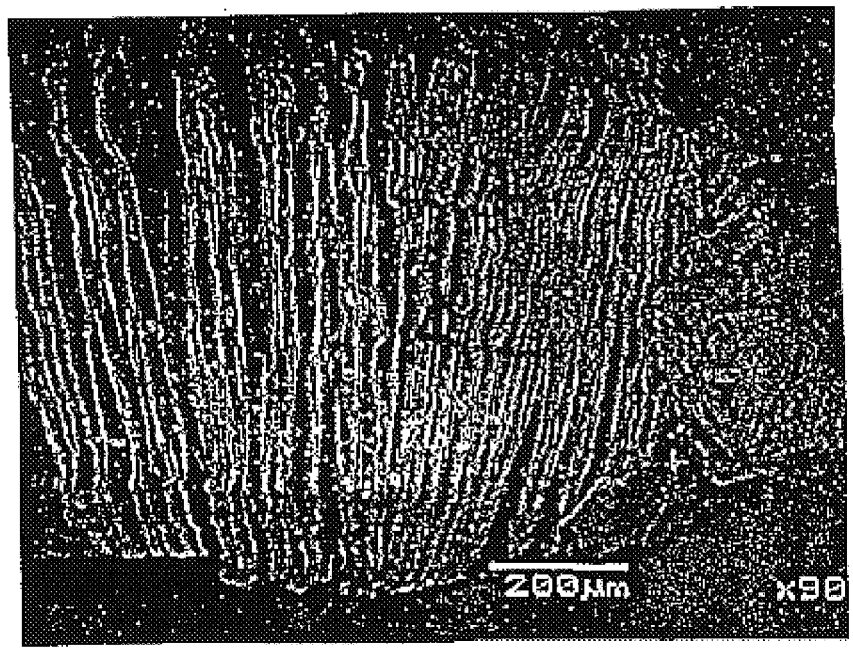
FIG. 11 is an exemplary x-ray diffraction photograph of vermiculite in Rinkite under conditions of heating.
Figure 12:
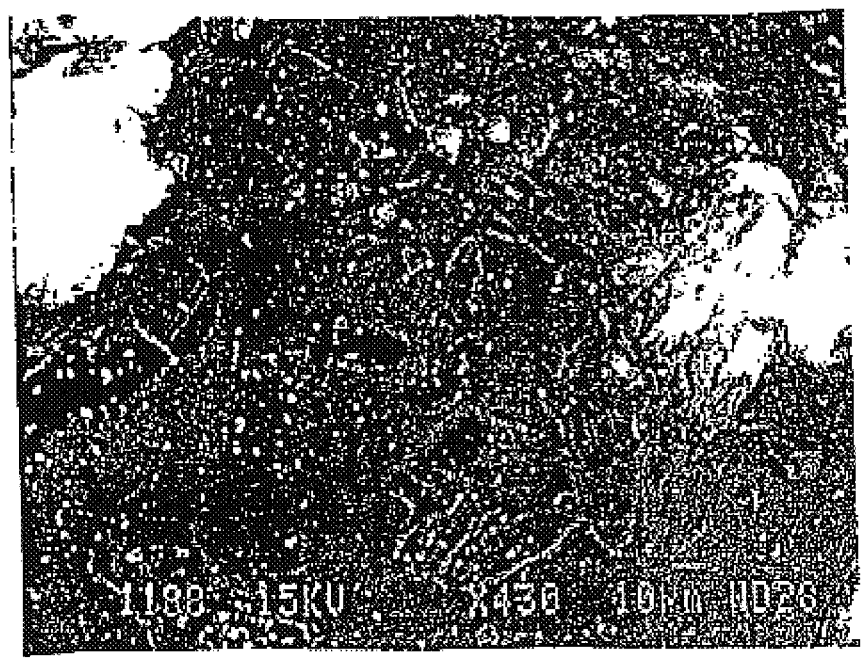
FIG. 12 is an exemplary secondary electron image of an iron particle in Rinkite.

Samples of the metamorphosed phlogopite were wet ground into a fine powder. The ground metamorphosed phlogopite samples were then slurry-mounted onto standard glass microscope slides for analysis. X-ray diffraction (XRD) analysis was conducted on samples. The XRD patterns were collected and the diffraction patterns were analyzed using a computer based search-and-match procedure with a database of known compounds. Results of XRD analysis of the metamorphosed phlogopite material identified hematite and phlogopite as major phases (see FIG. 8), while vermiculite (i.e., the metallic gold-colored particles inspected in the morphological analysis) was present as a minor phase (see FIG. 9). FIG. 10 illustrates the external morphology of the vermiculite particles and an iron-rich particle in the phlogopite sample. As illustrated in FIG. 11, the vermiculite particles show significant expansion upon heating (e.g., if at atmospheric pressure, to about 1500° F.). FIG. 12 is a secondary electron image of the surface of an iron particle in the phlogopite sample. The image of the particle offers evidence of a crystalline structure and illustrates some materials on the surface of the particle that form layers. These layers appear to shed from the surface of the particle, as evident on the rightmost side of the image in FIG. 12.

Applications for Use

Metamorphosed mineral compositions in accordance with various embodiments of the present invention may be utilized in any number of industrial, environmental, health and/or safety applications. Several exemplary embodiments of such applications are set forth in the following paragraphs; however, various other applications of the disclosed metamorphosed mineral compositions are indeed foreseeable in accordance with the present invention.

In accordance with one exemplary aspect, the subject invention relates to the use of metamorphosed mineral compositions, namely, metamorphosed phlogopite, in the control and/or reduction of $NO_x$ emissions from combustion gases as applied, for example, in a power plant exhaust system in order to comply with certain environmental discharge regulations or in other applications wherein control and/or reduction of emissions from exhaust gases, such as automobiles, is desirable. As used herein, the terms "control of emissions" and "reduction of emissions", or any variation thereof, are intended to include depleting, eliminating, reducing, transforming, adsorbing, absorbing, attracting, trapping, separating or otherwise partially or substantially altering the partition function of any particular gaseous chemical species from a mixture of at least two gaseous chemical species, which shall be properly regarded as within the scope and ambit of the present invention. It will be appreciated, however, that the principles of the present invention may be employed to ascertain and/or realize any number of other benefits associated with the control and/or reduction of emissions gases, including, but not limited to, the control and/or reduction of $SO_x$, the control and/or reduction of $CO_x$, the control and/or reduction of various other gaseous chemical species, the improved elimination or substantial reduction of harmful combustion gases in an automotive exhaust manifold, atmospheric control systems, personal breathing equipment control systems, and the reduction of the cost-of-ownership associated with certain equipment used in various settings to comply with environmental regulations.

In one exemplary embodiment of the present invention, metamorphosed phlogopite has demonstrated the ability to selectively and at least partially deplete certain chemical species from combustion exhaust gases, such as, for example, $SO_x$, $NO_x$, and $CO_x$. The metamorphosed phlogopite, in accordance with one exemplary application of the present invention, has a temperature dependency in its ability to de-$NO_x$ify and de-$SO_x$ify combustion gases. For example, at temperatures less than about 1200° F. to about 1600° F., that is, at temperatures below the mineral matter transformation temperature for phlogopite, and at a face velocity of about 5,000 volumes per hour (corresponding to about 1.38 feet per second for a metamorphosed phlogopite sample of given surface area), the reduction of $NO_x$ from the combustion gases produced at a commercial power plant test facility was observed to be about 90% efficient with respect to reduction of $NO_x$ and about 30% to about 40% efficient with respect to reduction of $SO_x$ from the combustion gases. Higher $NO_x$ and $SO_x$ reduction efficiencies are achievable at lower face velocities, that is, with slower gas stream velocities and/or larger sample surface areas.

Catalysts are materials that allow chemical reactions to take place, sometimes at milder conditions of, for example, temperature and-pressure, than would be required for the same chemical reactions to occur naturally. Redox reactions are specific reactions in which either reduction or oxidation occurs. The primary reactions noted in the use of metamorphosed mineral compositions in accordance with aspects of various embodiments of the present invention are reduction reactions wherein, for example, oxygen atoms are liberated from $NO_x$ and/or $SO_x$ molecular species to form molecular oxygen ($O_2$). Defect sites in or on the metamorphosed mineral composition of the present invention provide temporary sites for, for example, oxygen atoms to bond. This additional term in the kinetics equation permits the metamorphosed vermiculitic mica to operate at much lower temperatures than conventional catalysts. At conventional process temperatures, metamorphosed vermiculitic micas in accordance with the present invention have demonstrated redox reaction rates significantly higher than those associated with conventional catalysts.

Maghemite is a form of iron oxide, also known as $\gamma$-$Fe_2O_3$, with the crystalline structure of magnetite ($FeO.Fe_2O_3$) but the elemental composition of hematite ($Fe_2O_3$). Maghemite has been previously demonstrated to function as a catalyst. It is believed that super-oxides may be formed in vermiculite or phlogopite through the reaction of associated alkali and alkaline earth elements. This would result in the at least partial selective removal of oxygen from the $NO_x$ species in, for example, combustion flue gas to produce molecular nitrogen ($N_2$).

In accordance with an exemplary embodiment of the invention, metamorphosed vermiculitic mica formed in accordance with a preferred embodiment of the invention is used to control and/or reduce emissions of $NO_x$, $SO_x$, $CO_x$, and/or other undesirable gaseous components from combustion flue gases. In accordance with one aspect, metamorphosed vermiculitic mica is formed by heat treating a composite material comprising maghemite and phlogopite at a temperature of from about 1200° F. to about 1600° F. The metamorphosed vermiculitic mica is placed into a reaction vessel adapted to allow an exhaust gas to flow through the "bed" in a manner similar to a fluidized bed, a circulating bed or a filter. In accordance with a preferred aspect of this exemplary embodiment, the metamorphosed vermiculitic mica is first comminuted, then sieved to remove fine dust-making particles. The metamorphosed vermiculitic mica may be encapsulated inside a screen, filter, or such other suitable gas-permeable barrier to prevent the metamorphosed mica from being removed from the reaction vessel by the flow of gas. A typical application of this mode of device would be downstream of a particulate control device (in the case of, for example, a coal-fired unit) and may be configured for installation, for example, inside of existing ductwork in the case of most fossil fuel fired units.

In accordance with another exemplary embodiment of the invention, metamorphosed vermiculitic mica is used to control and/or reduce emissions of $NO_x$, $SO_x$, $CO_x$, and/or other undesirable gaseous components from industrial flue gases. In accordance with one aspect, metamorphosed vermiculitic mica is formed by heat treating a composite material comprising maghemite and phlogopite at a temperature of from about 1200° F. to about 1600° F. A suitable substrate, such as a steel sheet or plate, is fashioned so as to allow rolling gas contact across the surface of the substrate. In accordance with a preferred aspect of this exemplary embodiment, the design geometry of a chevron demister from, for example, a scrubber, may be used in fashioning a suitable substrate. The substrate may be covered with an adhesive, such as, for example, zirconium oxide glue or rubber cement. Any adhesive suitable to withstand the temperature and chemical environment of this exemplary application and that allows for the ability to regenerate the metamorphosed vermiculitic mica may also be used. The adhesive-covered surface may then be coated with comminuted metamorphosed vermiculitic mica material and allowed to set to adequately dry. The coating of comminuted metamorphosed vermiculitic mica material is preferably from about 1 to about 2 millimeters thick. Preferably, the setting/drying step is performed in an oven or other heated apparatus at approximately 200° F. for approximately 24 hours. After setting, multiple similarly-treated plates may be stacked and connected to form the finished device. For example, in accordance with a preferred aspect of this exemplary embodiment, two or more chevron plates may be stacked into a support frame adapted to enable flue gas to flow into and through the plates, thus allowing the metamorphosed vermiculitic mica to perform the desired treatment process. So fashioned, a treatment device containing metamorphosed vermiculitic mica or other suitable metamorphosed mineral composition in accordance with the present invention is effective for de-$NO_x$ification, de-$CO_x$ification, de-$SO_x$ification and other chemical control or reduction of undesirable gaseous components in the contacted flue gas. This exemplary embodiment of the present invention may easily be installed in, for example, existing baghouse compartments or in the ductwork sections downstream of a precipitator. In accordance with other exemplary embodiments of the invention, a pollution control device in an automobile may be formed using metamorphosed mineral composition media and various other principles of the invention. Pollution control and/or reduction devices for other applications also may be fabricated in accordance with the principles and aspects of the present invention, such as, for example, pollution control devices for wood, oil, and/or coal-burning stoves and furnaces, and a filter media for medical facilities that specifically deal with large volumes of $NO_x$, such as, for example, dentists' offices.

In accordance with another exemplary embodiment of the invention, metamorphosed mineral compositions formed in accordance with various aspects and embodiments of the present invention may be utilized in connection with the fabrication and use of chemical detectors, for example, as applied to the detection of carbon monoxide, nitric oxide, elemental chlorine, and elemental fluorine. Additionally, metamorphosed mineral compositions in accordance the present invention may be utilized in connection with the fabrication and use of chemical detectors for hydrochloric acid (HCl) and hydrofluoric acid (HF), which are common hazardous chemicals used in power plants, petroleum refineries, chemical manufacturing and processing plants, and other industrial facilities. Most facilities require some level of detection of such materials to protect the process, personnel, and the surrounding environment. The metamorphosed mineral compositions of the present invention are useful in connection with the fabrication of chemical detectors to detect the presence of specific materials in the environment, and are also suitable for use in respirator media to remove undesirable gaseous materials from the environment to make it safely breathable. It will be appreciated, however, that the principles of the present invention may be employed to ascertain and/or realize any number of other benefits associated with the detection of monatomic chemical species, including, but not limited to, carbon monoxide, nitric oxide, elemental chlorine, elemental fluorine, hydrochloric acid, hydrofluoric acid, and other gaseous compounds. The principles of the present invention may also be applied to reduce the cost-of-ownership associated with chemical detection equipment used in various settings such as, for example, to measure concentrations of certain monatomic chemical species and/or to detect harmful chemicals in security or environmental monitoring applications.

In accordance with yet a further exemplary application of the present invention, a new method for the fabrication and manufacture of feature-scale chemical detection devices is provided involving a highly selective means for introducing, for example, binary resistive bridges into a crystal lattice. In accordance with one representative aspect of the present invention, a metamorphosed mineral composition, such as, for example, metamorphosed phlogopite, may be obtained in accordance with any of the methods herein disclosed, for example, by mixing a suitable quantity of phlogopite with a suitable quantity of maghemite (or any other suitably adapted oxidation inhibitor) and heat treating the composition at a temperature of at least about 90% of the mineral matter transformation temperature of the combination. As mineral matter transformation occurs, oxygen atoms are at least partially depleted from the crystal lattice of the phlogopite, creating monatomic defects in the crystal lattice. These defects form areas to which monatomically bonded oxygen atoms have an affinity, and a sensor device is thus formed thereby. For example, if these monatomic defects were to be bounded by some other material sensing the resistance across such a sensor bridge, the temporary addition of oxygen atoms would alter the resistance value of the bridge, for example, giving the bridge a higher resistance. Accordingly, feature-scale devices could be incorporated into the crystal lattice of the metamorphosed mineral composition to operate as sensors, for example, to detect molecules that are monatomically bonded to oxygen. The present invention could be further applied, for example, as a replacement to existing technology for detecting certain gases, such as, for example, $O_3$, $CO_x$, radon, $SO_x$, $NO_x$ and the like, or in any other application now known or hereafter derived by those skilled in the art for highly selective and/or highly sensitive detection of monatomic chemical species. Detector applications, in accordance with various exemplary applications of the present invention, need not necessarily be limited to the utilization of oxygen defects. Use of a scavenger for sulfur, chlorine, fluorine, or other chemical species in the production of metamorphosed mineral compositions in accordance with the various aspects and embodiments of the present invention would yield feature-scale detection devices selectively sensitive to the corresponding depleted species. Moreover, because of the high level of controllability and precision of the methods of the present invention in creating specifically-engineering monatomic defects, such feature-scale detection devices are distributable throughout the crystal lattice of a suitable mineral composition to produce a matrix detection device that may be suitably adapted to detect a variety of monatomic chemical species sequentially, non-sequentially, simultaneously, randomly, in a cascade and/or any other isotropic or anisotropic chronometric sequence now known or hereafter derived by those skilled in the art.

In accordance with yet a further exemplary aspect, the subject invention relates to metamorphosed mineral compositions such as, for example, metamorphosed vermiculitic mica, useful in the manufacture of solid-state devices, for example, as applied to the fabrication of integrated circuits. It will be appreciated, however, that the principles of the present invention may be employed to ascertain and/or realize any number of other benefits associated with the manufacture of solid state devices, including, but not limited to, detectors for gaseous $NO_x$, $SO_x$ and/or $CO_x$, as well as improvement of quantum dot semiconductor technology and/or the manufacture of discrete electronic components.

Most solid-state devices are manufactured by starting with a substantially pure silicon substrate and/or undoped semiconductor material layer. Active sites are built-up or introduced into the material by the introduction of impurities such as, for example, arsenic. These active sites give solid-state devices their P or N electron mobility properties for the subsequent fabrication of transistors and integrated circuits. By starting with a crystalline material and removing atoms without substantially changing the lattice geometry, defects may be introduced that may be dictated by the geometry of the crystal. This results in defects that conform to a geometry much more precisely than conventional solid-state device fabrication techniques.

In accordance with such an exemplary application of the present invention, a new method for the fabrication and manufacture of solid state devices is provided involving, inter alia, a highly selective means for introducing dopants into a semiconductor lattice. In one representative aspect, metamorphosed phlogopite may be obtained in accordance with any of the methods herein disclosed, for example, by mixing a suitable quantity of phlogopite with a suitable quantity of maghemite (or any other suitably adapted oxidation inhibitor) and heat treating the composition at a temperature of at least about 90% of the mineral matter transformation temperature of the combination. As mineral matter transformation occurs, oxygen atoms are at least partially depleted from the crystal lattice of the phlogopite, creating monatomic defects in the crystal lattice. As the defects are formed through the metamorphic process, and as a suitable number of oxygen atom defects are introduced into the silicon matrix, the silicon lattice is left with silicon bounded with silicon dioxide. These silicon substrates are bounded by the electrically insulative silica, but may comprise, for example, a silicon strip. If an appropriate valence material were thereafter removed (leaving behind silicon and the defect), the silicon matrix would be suitably adapted to function as either an N-doped or P-doped solid state device. Such silicon lattice defects allow, inter alia, for a wider range of positive and/or negative doping valences. It is further considered that since these defects are on the order of magnitude of Planck's constant, the defects would likely be of substantial utility to complement quantum dot applications currently under development in the semiconductor industry.

In the foregoing description, the invention has been described with reference to specific embodiments. However, it will be appreciated that various modifications and changes may be made without departing from the scope of the present invention as set forth herein. The description and figures are to be regarded in an illustrative manner, rather than a restrictive one, and all such modifications are intended to be included within the scope of the present invention. Accordingly, the scope of the invention should be determined by the disclosed compositions, methods and/or technologies and their legal equivalents, rather than by merely the examples given above. For example, the steps recited in any of the method or process steps may be executed in any order and are not limited to the order presented herein.

Benefits, other advantages, and solutions to problems have been described above with regard to specific embodiments. However, the benefits, advantages, solutions to problems, and any element(s) that may cause any benefit, advantage, or solution to occur or become more pronounced are not to be construed as critical, required, or essential features or elements of the invention herein described. As used herein, the terms "comprises", "comprising", or any variation thereof, are intended to cover a non-exclusive inclusion, such that a process, method, article, composition of matter or apparatus that comprises a list of elements does not include only those elements but may include other elements not expressly listed or inherent to such process, method, article, composition of matter or apparatus. Other combinations and/or modifications of the above-described compositions, structures, arrangements, applications, proportions, elements, materials or components used in the practice of the present invention, in addition to those not specifically recited, may be varied or otherwise particularly adapted by those skilled in the art to specific environments, manufacturing or design parameters or other operating requirements without departing from the general principles of the same.

What is claimed is:

1. A method of forming metamorphosed mineral composition having internal lattice defects, comprising:
   providing a composite material stream, said composite material stream comprising:
      from about 5% by weight to about 50% by weight of a scavenger material, and
      from about 50% by weight to about 95% by weight of a mineral composition, wherein said mineral composition has a mineral matter transformation temperature; and
   heat treating said composite material stream at a temperature of at least about 90% of the mineral matter transformation temperature for the mineral composition in an environment having less than about 5% excess oxygen.

2. The method of claim 1, wherein said step of providing a composite material stream comprises providing a composite material stream comprising from about 5% to about 40% by weight of said scavenger material.

3. The method of claim 1, wherein said step of providing a composite material stream comprises providing a composite material stream comprising from about 10% to about 30% by weight of said scavenger material.

4. The method of claim 1, wherein said step of providing a composite material stream comprises providing a composite material stream comprising from about 70% to about 90% by weight of said mineral composition.

5. The method of claim 1, wherein said step of providing a composite material stream comprises providing a composite material stream comprising at least one of an oxygen scavenger and a halide scavenger.

6. The method of claim 1, wherein said step of providing a composite material stream comprises providing a composite material stream comprising at least one of hematite, elemental carbon, silicon, an aluminum silicate, and mixtures thereof.

7. The method of claim 1, wherein said step of providing a composite material stream comprises providing a composite material stream comprising at least one of vermiculite, phlogopite, mica, biotite, ganterite, and mixtures thereof.

8. The method of claim 1, wherein said step of heat treating said composite material stream in an environment having less than bout 5% excess oxygen comprises heat treating said composite material stream under conditions of at least partial vacuum.

9. The method of claim 1, wherein said step of heat treating said composite material stream in an environment having less than bout 5% excess oxygen comprises heat treating said composite material stream in the presence of an inert gas stream.

10. The method of claim 1, further comprising the step of comminuting said composite material stream prior to said step of heat treating said composite material stream.

11. The method of claim 1, further comprising the step of comminuting said scavenger material prior to said step of providing said composite material stream.

12. The method of claim 1, further comprising the step of comminuting said mineral composition prior to said step of providing said composite material stream.

13. A method of forming metamorphosed vermiculitic mica having internal lattice defects, comprising:
   providing a composite material stream, said composite material stream comprising:
      from about 5% by weight to about 50% by weight of a scavenger material, said scavenger material comprising at least one of an oxygen or a halide scavenger;
      from about 50% by weight to about 95% by weight of a vermiculitic precursor material; and
   heat treating said composite material stream at a temperature of at least about 90% of the mineral matter transformation temperature for the vermiculitic precursor material in an environment having less than about 5% excess oxygen.

14. The method of claim 13, wherein said step of providing a composite material stream comprises providing a composite material stream comprising from about 5% to about 40% by weight of said scavenger material.

15. The method of claim 13, wherein said step of providing a composite material stream comprises providing a composite material stream comprising from about 10% to about 30% by weight of said scavenger material.

16. The method of claim 13, wherein said step of providing a composite material stream comprises providing a composite material stream comprising from about 70% to about 90% by weight of said vermiculitic precursor material.

17. The method of claim 13, wherein said step of providing a composite material stream comprises providing a composite material stream comprising at least one of hematite, elemental carbon, silicon, an aluminum silicate, and mixtures thereof.

18. The method of claim 13, wherein said step of providing a composite material stream comprises providing a composite material stream comprising at least one of vermiculite, phlogopite, mica, biotite, ganterite, and mixtures thereof.

19. The method of claim 13, wherein said step of heat treating said composite material stream in an environment having less than about 5% excess oxygen comprises heat treating said composite material stream under conditions of at least partial vacuum.

20. The method of claim 13, wherein said step of heat treating said composite material stream in an environment having less than bout 5% excess oxygen comprises heat treating said composite material stream in the presence of an inert gas stream.

21. The method of claim 13, further comprising the step of comminuting said composite material stream prior to said step of heat treating said composite material stream.

22. The method of claim 13, further comprising the step of comminuting said scavenger material prior to said step of providing said composite material stream.

23. The method of claim 13, further comprising the step of comminuting said vermiculitic precursor material prior to said step of providing said composite material stream.

24. A method of forming metamorphosed phlogopite having internal lattice defects, comprising:
   providing a composite material stream, said composite material stream comprising:
      from about 5% by weight to about 50% by weight of maghemite;
      from about 50% by weight to about 95% by weight of phlogopite; and
   heat treating said composite material stream at a temperature of from about 1200° F. to about 1600° F. in an environment having less than about 5% excess oxygen.

25. The method of claim 24, further comprising the step of comminuting said composite material stream prior to said step of heat treating said composite material stream.

26. The method of claim 24, further comprising the step of comminuting said maghemite prior to said step of providing said composite material stream.

27. The method of claim 24, further comprising the step of comminuting said phlogopite prior to said step of providing said composite material stream.

28. The method of claim 24, wherein said step of heat treating said composite material stream in an environment having less than about 5% excess oxygen comprises heat treating said composite material stream under conditions of at least partial vacuum.

29. The method of claim 24, wherein said step of heat treating said composite material stream in an environment having less than about 5% excess oxygen comprises heat treating said composite material stream in the presence of an inert gas stream.

30. A metamorphosed mineral composition comprising:
   from about 5% by weight to about 50% by weight of a scavenger material,
   from about 50% by weight to about 95% by weight of a mineral composition; and
   an effective number of monatomic defects in the crystal lattice.

31. The composition of claim 30, wherein said scavenger material comprises at least one of an oxygen scavenger and a halide scavenger.

32. The composition of claim 30, wherein said scavenger material comprises at least one of hematite, elemental carbon, silicon, an aluminum silicate, and mixtures thereof.

33. The composition of claim 30, wherein said mineral composition comprises at least one of vermiculite, phlogopite, mica, biotite, ganterite, and mixtures thereof.

34. The composition of claim 30, wherein said scavenger material comprises from about 5% to about 40% by weight of said metamorphosed mineral composition.

35. The composition of claim 30, wherein said scavenger material comprises from about 10% to about 30% by weight of said metamorphosed mineral composition.

36. The composition of claim 30, wherein said mineral composition comprises from about 70% to about 90% by weight of said metamorphosed mineral composition.

37. The composition of claim 30, wherein said effective number of monatomic defects comprises at least about 2% by volume of said crystal lattice of said metamorphosed mineral composition.

38. The composition of claim 30, wherein said effective number of monatomic defects comprises from about 2% to about 10% by volume of said crystal lattice of said metamorphosed mineral composition.

39. The composition of claim 30, wherein said effective number of monatomic defects comprises from about 3% to about 8% by volume of said crystal lattice of said metamorphosed mineral composition.

* * * * *